| United States Patent [19] | [11] Patent Number: 4,767,785 |
| Georgieff | [45] Date of Patent: Aug. 30, 1988 |

[54] HYPOCALORIC PREPARATION AND INTRAVENOUS METHOD FOR HYPOCALORIC TREATMENT OF PATIENTS

[76] Inventor: Michael Georgieff, 22 Gleiwitzer Str., Hemsbach, Fed. Rep. of Germany, 6944

[21] Appl. No.: 935,120

[22] Filed: Nov. 26, 1986

Related U.S. Application Data

[63] Continuation of Ser. No. 712,275, Mar. 15, 1985, abandoned, which is a continuation-in-part of Ser. No. 572,215, Jan. 18, 1984, abandoned.

[51] Int. Cl.$^4$ .......................................... A61N 31/195
[52] U.S. Cl. ..................................... 514/561; 514/562
[58] Field of Search ................................ 514/561, 562

[56] References Cited

U.S. PATENT DOCUMENTS

| 3,152,955 | 10/1964 | Gans et al. | 424/319 |
| 3,793,450 | 2/1974 | Schnell | 424/319 |
| 4,357,343 | 11/1982 | Madsen et al. | 424/319 |

OTHER PUBLICATIONS

Chem. Abs. 218617x (1983).

*Primary Examiner*—Stanley J. Friedman
*Attorney, Agent, or Firm*—Donald Brown

[57] ABSTRACT

Isotonic hypocaloric preparation comprising essential dietary amino acids with or without nonessential dietary amino adies, and xylitol, and method of treating patients ill from renal failure, cancer cachexia and receiving respiratory therapy.

3 Claims, No Drawings

HYPOCALORIC PREPARATION AND INTRAVENOUS METHOD FOR HYPOCALORIC TREATMENT OF PATIENTS

PRIOR APPLICATION

This application is a continuation of application Ser. No. 712,275, filed Mar. 15, 1985, now abandoned, which is a continuation-in-part of U.S. patent application Ser. No. 572,215, filed Jan. 18, 1984, now abandoned.

BACKGROUND OF THE INVENTION

This invention relates to a method of peripheral venous treatment of a mammals e.g., patients (human or animal) who suffers from renal disease, cancer cachexia and those receiving ventilatory support. More specifically, it relates to xylitol as the sole carbohydrate which together with amino acids in the absence of fat emulsions is used for peripheral vein administration and will unexpectedly preserve body protein in above mentioned patients.

A hypocaloric preparation provides 400 to 1200k cal per day which delivers less than the patient's total needs and is usually accomplished with peripheral glucose which sometimes includes amino acids. Hypercaloric preparations provide 1500 up to 10,000k cal per day. The present invention is unexpectedly superior to current hypocaloric regimens of carbohydrates with or without amino acids.

In renal failure and cancer cachexia insulin resistance and elevated catabolic hormones result in a net release of amino acids, primarily from muscle and connective tissue, but also from kidney and gastrointestinal mucosa. The increased extracellular amino acid pool is associated with an enhanced gluconeogenesis in the liver to meet the requirements of those tissues that can use only glucose. In addition, there is an increased synthesis of fibrinogen and acute phase globulins in the liver (Blackburn, G. L., Phinney, S. D., in *Surgical Physiology*, ed. Burke, J. F., Philadelphia, C. V. Mosby and Co., 1980) as well as an accelerated protein synthesis rate in the cellular immune system (Gross, R. L., Newberne, P. M. *Physiol. Rev.*, 60, 188, 1980). Mobilization of fatty acids aids in fulfulling the energy requirements of the liver. Despite augmented fatty acid oxidation, fewer ketone bodies are formed to serve as an alternative energy source for heart, skeletal muscle, brain, and kidney.

Even hypocaloric glucose infusions reduce fatty acid oxidation and ketone body production. The failure of ketone body production in the liver contributes to a severe energy deficit in muscle tissue, which may lead to an accelerated proteolysis. Since skeletal muscle constitutes about 40 percent of body mas, the metabolism of muscle tissue plays a major role in the mobilization and oxidation of amino acids in the periphery. Branched chain amino acids and intermediates of some dispensible amino acids are oxidized in skeletal muscle to fulfill the energy deficit and to provide nitrogen groups and carbon skeletons for the synthesis of alanine and glutamine. These two amino acids are then released at rates greater than their concentration in muscle tissue, and the increased availability to gluconeogenic substrates, mainly alanine, advanes glucose production in the liver. Glucose given even in small quantities (150–300 g/day) as a component of parenteral nutrition therapies can be deleterious to the liver in such a situation, because it cannot reduce gluconeogenesis (Long, C. L., Jeevanandam, M., Kim, B. M., Kinney, J. M., *Am. J. Clin. Nutr.*, 30, 1340, 1977) but rather stimulate lipogenesis. The use of hypertonic carbohydrate mixtures which are exclusively for central venous administration are frequently used in clinical practice and consist of glucose, fructose, and xylitol in a preparation of 1:1:1 at a total dosage of 600 g/day (Georgieff, M., Geiger, K., Bratsch, H. et al. in *Recent Advances in Clinical Nutrition I*, ed. Howard, A., Baird, J., Mc.L., John Libbey and Company, Ltd, 1981). Glucose in these solutions is reported to stimulate hepatic lipogenesis. It has been observed that using xylitol for hypercaloric use in hypertonic preparations is no better than using only glucose.

In liver tissue, glucose-6-P is metabolized by 4 main metabolic pathways.

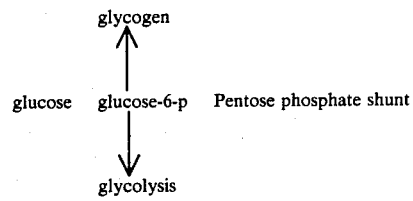

After an oral glucose meal, only 20–30% of the glucose taken up by liver is directly oxidized while the rest is converted to glycogen or triglycerides and then secreted as very low density lipoprotein-triglycerides (VLDL-TG). During continuous high carbohydrate intakes such as in currently available total parenteral nutrition regimens, the amount of glucose being metabolized in the glycolytic pathway and converted to VLDL-TG is increased, due to an activation of the enzymes involved in that process. The amount of glucose metabolized in the pentose phosphate shunt varies from 10 to over 30% of total liver glucose uptake. In this cycle ribose and deoxyribose are synthesized for the formation of nucleic acid, the initial step of protein synthesis (Newsholme, E. A., and Start, C., *Regulation in Metabolism*, John Wiley and Sons, London, New York, Sydney, Toronto, 1976). after illness the rate of glucose oxidized via the pentose phosphate shunt is more than doubled (Wannemacher, R. W., Jr., Beall, F. A., Canonico, P. G., et al., *Metabolism*, 29, 201, 1980). A large amount of glucose derived from amino acids during the process of gluconeogenesis after trauma enters this pathway thus contributing to the loss of protein.

During prolonged periods of illness like renal failure, cancer and respiratory therapy and notwithstanding conventional intravenous feeding, a significant loss of body weight is often observed. Of major concern to all in this field of nutritional support is the loss in body mass, i.e., muscle, organs, etc. This loss correlates to a loss of body nitrogen. When amino acids originating from lean body mass are converted to glucose in the liver, urea is generated and excreted in the urine. The determination of urinary urea-nitrogen content can, therefore, indicate a decrease in lean body mass. By measuring nitrogen intake and output, a nitrogen balance can be made. A nitrogen excretion exceeding the intake is often seen after trauma, sepsis, and other severe illness and can result in morbidity, even mortality. Protein depletion, particularly of visceral organs, represents the single most important unresolved aspect of illness today. A loss of 30% of the original body weight during intravenous feeding in a seriously ill patient very often leads to death (Hadley, H. D., "Percent of Weight Loss: A Basic Indicator of Surgical Risk", *Journal American Medical Assoc.*, 106, 458, 19 and Taylor and Keyes, "Criteria of Physical Fitness in Negative Nitrogen Balance", *Ann. N.Y. Acad. Sc.*, 73, 465, 1958).

Attempts at feeding patients intravenously are complicated because the intravenous route represents an abnormal method of administering nutrients in the body. During oral food intake, the hepatic portal vein drains most of the absorption area of the gut so that apart from long chain triglycerides, which are taken up via the thoracic lymph duct, dietary nutrients are absorbed via the portal vein (Havel, R. J., *N. Engl. J. Med.*, 287, 1186, 1972). Most compounds that are absorbed from the gut pass through the liver, and therefore, the liver is forceably situated to function as the initial regulator of the blood systemic level of many compounds that enter the body through the gut. This regulating function of the liver is especially important regarding glucose uptake and utilization. After an oral carbohydrate containing meal, glucose concentrations in the portal blood increase from about 5 to 40 mM or more while peripheral blood glucose concentrations range only from 4 to maximally 10 mM. The ability of the liver to remove glucose from the portal blood is guaranteed by an enzyme, glucokinase, which is only found in the liver.

Glucokinase activity is regulated by portal venous glucose and insulin levels. In contrast to oral food intakes, during intravenous glucose infusions, portal venous blood glucose concentrations do not reach high peak levels as after oral uptake and glucokinase activity remains relatively low (Jshida, T., Chap., S., Chuo, J., Lewis, R., Hartley, C., et al., *J. Clin. Invest.*, 72, 590, 1983) so that liver is not capable in functioning as a buffer for glucose homeostasis. Therefore, during an intravenous glucose infusion, as is observed during standard parenteral nutrition feedings, the delicate interrelationship between substrates transported in the blood and their effect upon intermediary metabolism in various organs is determined by unphysiologically high systemic blood glucose and insulin levels. In contrast, the object of the present invention is the use of xylitol and amino acids to provide the patient with an energy source which is converted in the liver to glucose so that during intravenous feeding the liver can again regulate glucose homestasis.

Although the most frequently used carbohydrate for intravenous feeding is glucose, recent studies have demonstrated that hepatic glucose output is substantially diminished by the infusion of 0.06 to 0.12 gm glucose per kilogram per hour (100-200 g/day). Intravenous administration of glucose above the endogenous synthesis rate causes only a marginal further reduction in endogenous glucose production. Under optimal conditions, only 30 percent of glucose entering the liver is directly oxidized; the remainder is converted to glycogen or fat. The percentage of glucose oxidized declines above an infusion rate of 0.12 gm per kilogram per hour (Wolfe, R. R., Allsop, J. R., Burke, J. F., *Metabolism*, 28, 210, 1979).

During intravenous infusion of 600 gm glucose together with amino acids, approximately 130 gm of triglyceride are synthesized in the liver. These triglycerides are bound to lipoproteins and relesed as VLDL triglycerides. The rate-limiting step during hepatic lipogenesis is not the conversion of glucose to fatty acids and the esterification to triglycerides, but the incorporation of triglycerides into the VLDL fraction. It is easily understood that continuous intravenous glucose infusion at high rates will exceed the capacity of the liver to synthesize VLDL triglycerides. The accumulation of triglycerides results in periportal fatty infiltration and a rise of liver specific enzymes.

Large intravenous doses of glucose also produce hyperglycemia and hyperinsulinemia. An increase in secretion of insulin and to a greater extent, the administration of exogenous insulin reduces muscle catabolism, thereby improving nitrogen balance. Under these circumstances, protein synthesis is shifted to the peripheral organs, mainly to muscle tissue (Woolfson, A. M. J., N. Engl., *J. Med.*, 300, 14, 1979). Intravenous administration of glucose in excess of 0.06 g/kg BW.h (100 g/day) results in a progressive decline of total protein, albumin, pre-albumin, retinol-binding protein, and transferring (Loehlein, D., Zick, R., *Infusions therapy*, 8, 133, 1981) concentrations.

Because intravenously administered glucose bypasses the liver, the organ of blood glucose homeostasis, even rates of 0.12 gm per kilogram per hour are associated with a significant increase in blood glucose and insulin levels in ill patients. (Elwyn, D. H., Kinney, J. M., Jeevanadam et al., *Ann. Surg.*, 190, 177, 1979). Most important, however, gluconeogenesis and the concomitant loss of lean body mass is not reduced. As the gut mucosa also contributes to protein wasting by increasingly releasing amino acids during illness, any intravenous nutritional therapy not reducing protein wasting, will simultaneously prolong the availability of adequate oral nutrient uptake, which is unquestionably the most efficient route for feeding a patient.

In contrast to the present art, a goal of this invention in feeding the patient with renal failure, respiratory therapy and cancer cachexia is to moderate blood glucose and insulin elevations and to attenuate the loss of lean body mass by reducing gluconeogenesis. Xylitol oxidation is insulin independent without hyperglycemia (DeKalermatten, N., Ravussin, E., Maeder, E., et al., *Metabolism*, 29, 62, 1980). It enters the pentose phosphate shunt directly and does not require insulin. The maximal turnover capacity is elevated during illness in contrast to glucose. Maximal xylitol disposal rate in man during normal metabolic conditions is 0.37 g/kg BW.h (620 g/day). Depending on the severity of an illness, the maximal disposal rate may increase to 0.6 g/kg BW.h (1000.0 g/day) and 0.76 g/kg BW.h (1277 g/day) (Ackermann, R. H., *Infusion Therapie*, 7, 113, 1980) respectively. In contrast to xylitol, maximal glucose disposal rates after illness are reduced by approximately 36% from 1440 g/day to 925 g/day, even supraphysiologic insulin concentrations are not capable of increasing the limit during illness (Black, P. R., Brooks, D. C., Bessey, P. Q. et al., *Ann. Surg.*, 196, 420, 1982). Unlike, glucose, intravenously administered xylitol is primarily metabolized in the liver and there converted to glucose independent of insulin. (Pellaton, M., Acheson, K., Maeder, E. et al., *JPEN*, 2, 627, 1978).

Insulin concentrations higher than basal levels are not needed for utilization of xylitol when infused at low rates of 0.08-0.1 g/kg BW.h (125-185 g/day). At these infusion rates xylitol not only will not stimulate insulin release but also will not require insulin to be metabolized to the triose part of the glycolytic pathway. Insulin, however, is needed for further metabolism. Thus, the generation of glucose-6-phosphate in the liver cells requires far less insulin than that required for the activation of glucose.

Previous studies have shown that during long term infusion of xylitol alone at a rate of 0.125 g/kg BW.h (210 g/day) in healthy volunteers, blood glucose levels actually decrease, due to reduced gluconeogenesis, since during its intravenous infusion, xylitol leads to a higher glycogen deposition than glucose, and glycogen is one of the most potent inhibitors of gluconeogenesis. In addition, the concentration of insulin needed for preventing gluconeogenesis is likely to be much lower than that needed for the activation of glucose in the liver cell.

At present, xylitol has either only been used as part of hypertonic carbohydrate mixture solution consisting of glucose, fructose, xylitol in preparation of 200 g/200 g/200 g with a total intake of 600 g/per day or given to unstressed or only mildly stressed patients. The presently available xylitol and amino acid mixture solution is only to be used as a part of a hypercaloric infusion regimen. This xylitol/amino acid solution also contains electrolytes, is hypertonic, and cannot be given into a peripheral vein. The ability of peripherally administerably xylitol and amino acid solution to preserve protein in a patient suffering from renal failure, cancer cachexia or undergoing respiratory therapy and in fact would be unexpected from the prior art. The use of hypertonic xylitol together with amino acids in elective surgery patients in contrast results in significantly higher nitrogen excretion in the urine and is thus not protein sparing and in fact caused larger amounts of protein wasting because of the large amino acid amounts administered (Georgieff, M., Kattermann, R., Geiger, K., et al., *Infusions Therapie*, 2, 69, 1981). Therefore, the art concerning xylitol and amino acid preparations suggests that such infusions would not be useful in critically ill patients.

It is the object of the present invention to provide an energy source which can be used together with amino acids for a patient obliged to receive nutritional requirements via parenteral administration to optimize the nutritional regimen. In this regard, it is an object to provide an energy source which is compatible for prolonged use in the substrate homeostasis which results in nitrogen-sparing of a patient who is suffering from renal failure, cancer cachexia and respiratory therapy and which will promote host defense, immune competence, non-sepsis, fast resumption of oral nutrient intake, and survival of the patient.* This goal is obtained through this invention, in which a novel preparation and a method of administering it is disclosed to support the above mentioned ill patient and reduce protein-wasting and gluconeogenesis by using isotonic hypocaloric preparations of xylitol and amino acids which together reduce protein wasting and supporting hepatic protein synthesis and function. This combination results in an unexpected improvement of nitrogen balance in contrast to giving xylitol or the amino acids alone.

*My invention uses specifically less of both xylitol and amino acids and surprisingly results in a product which cannot only administered in a peripherial vein but more importantly in a product which spares protein (i.e., Nitrogen sparing).

STATEMENT OF THE INVENTION

The invention described herein is a novel parenteral nutrition solution made from amino acids and xylitol, and a method of treatment employing it for use in a patient suffering renal disease cancer, cachexia and respiratory therapy to reduce nitrogen wasting and its accelerated gluconeogenesis. The novel solution of the invention is comprised of an aqueous amino acid and xylitol solution suitable for peripheral venous administration (infusion) in which the total amino acid content is between 10–80 g/l, preferably 35 to 50 g/l, most preferably about 35 g/l and the xylitol is between 10–80 g/l, preferably 30 to 80 g/l, most preferably about 50 g/l and can be sterilized by head without the occurence of a Maillard reaction. Most preferably, this novel solution is presented in a form in which the osmolality is between 300–900 mOsm which is safe for both peripheral and central venous injection.

The invention described herein is based partly upon the recognition that reducing the wasting of tissue protein and gluconeogenesis are critical to effective and successful recovery. Accordingly, an increased fatty acid oxidation and ketogenesis will reduce the obligatory need to a catabolize tissue protein for energy and therefore provide more precursors for wound healing, leukocytosis and hepatic secretory protein synthesis, essential for recovery.

That such a nutritional regimen could reduce nitrogen wasting and promote hepatic secretory protein synthesis, and in turn recovery is not only surprising but is also a radical departure from the art. That is, the newly discovered pharmacologic effect of hypocaloric amino acid and xylitol solutions of the present invention, specifically that such a solution will uniquely reduce gluconeogenesis and protein wasting, is highly surprising since xylitol has always been assumed to be a non-important calorie source in hospitalized patients that can be toxic at high intakes. Indeed at intakes of greater than 210 g xylitol/dy, excessive losses occur in the urine associated with increased losses of potassium which can lead to cardiac arrhythmias, metabolic alkalosis and death. Oxaloacelate deposition in kidney and brain has also been ascribed to excesive xylitol intakes, which has further led to the belief that administration of such a nutrient in appreciable quantities to above mentioned patients is contraindicated. Intakes of xylitol greater than 400 g/day are associated with increased uric acid production due to depletion of hepatic high energy phosphates subsequently leading to increased liver specific enzymes and bilirubin, inductive of hepatic dysfunction.

Previous investigations of amino acid and xylitol solutions have: (1) recommended xylitol intakes of less than 210 g/day, (2) recommended the addition of other carbohydrate sources (glucose, fructose, sorbitol, maltose) to be administered in a hypercaloric regimen via central venous injection and (3) demonstrated in mildly injured patients, no unique efficacy of xylitol solutions when compared to other carohydrate sources. This invention is based in part on newly discovered aspects of the body's response to serious illness, involving a failure to other common intravenous nutrients to reduce protein wasting and gluconeogenesis.

The novel intravenous solution of the present invention, and its use, provide a significant advance over known infusion solutions and known nutritional therapies in reducing protein wasting and supporting recovery. While it is known in the art that xylitol and amino acids preparations of this invention have anti-catabolic properties, it is highly surprising that such a solution could reduce urinary nitrogen loss, increase fat oxidation and ketogenesis and increase hepatic protein synthesis in a ill patient to such a degree, and thus promote and even optimize host defense and survival.

This invention is particularly useful for ill patients who require ventilatory support. The intermittant positive pressure breathing during surgery and ventilatory support can result in up to a 45% reduction in hepatic blood flow. Patients who receive continuous positive pressure ventilation especially with positive and expiratory pressure (PEEP) have extremely high rates (greater than 75%) of hepatic dysfunction secondary to reduced blood flow. This reduced blood flow coupled with standard nutrition regimens containing glucose leads inevitably to central lobular lipid deposition in the liver and serious hepatic disease. In contrast, the novel solution and method of this invention can uniquely reduce fatty liver and subsequent hepatic dysfunction. In such a patient population, the administration of fat emulsions is contraindicated because fat emulsions can enhance the already deteriorated lung function by occluding the pulmonary vessels.

Efficiency is of critical importance in this regard. Although a hypertonic (only suitable for central venous administration) amino acid and xylitol preparation is currently on the market, (LXA ®, Boehringer-Mannheim Salvia, Mannheim, FRG) (it contains 8% amino acids, 12.5% xylitol and additional electrolytes), the product, due to its extreme hypertonicity is limited to central venous injections and specifies on its product insert its use only with additional glucoe and fructose calories to deliver all of the patient's calorie needs. Central venous catheterization in a patient is a serious surgical procedure and carries an overall complication rate of 12%. This invention teaches that such hypertonic multi-nutrient regimens to be administered by central venous injection are unnecessary in ill patients and that a solution of amino acids and xylitol which can be given safely through a peripheral vein can unexpectedly better support the ill patient. The novel formula and solution of the present invention obviates some of the adverse side effects of current nutritional therapies by moderating the blood blucose and insulin increases seen with current glucose-containing solutions which increase resting energy expenditure and promote hepatic lipogenesis. Such a novel invention also increases endogenous fat oxidation and reduces carbon dioxide production as well as lipoprotein synthesis.

In view of the limitations on the amount of nutritional support which can be provided to a patient, it is typically impossible to replace all of the normal nutritional intake of a ill patient. In that situation, it becomes vitally important to administer a nutritional therapy which most efficiently reduces tissue protein loss. In many smaller hospitals, pharmacies are not well equipped to manufacture special solutons to such critically ill patients, and physicians do not routinely use central venous injections for nutritional support. This invention offers a substantial benefit in that it can be manufactuered and sterilized by standard techniques with an extended shelf-life without the formation of browning products due to the Maillard reaction. Such an invention would offer a substantial benefit to smaller institutions since it could be obtained in bulk from a central supplier and administered by standard peripheral vein infusion.

This invention relates to the use of xylitol with amino acids in order to support protein retention in ill patients. The amino acids contained in this invention are all normally administered for protein synthesis, although some can be synthesized by the body. Therefore the amino acids which will normally be included are those which the body does not synthesize are called dietary essential amino acids. Dietary essential amino acids are defined as those which cannot be synthesized by the body and must be either orally consumed or administered. These include L-isoleucine, L-leucine, L-valine, L-tryptophan, L-phenylalinine, L-lysine, L-methionine, L-threonine and in renal disease, L-histadine. See Biochemistry, Kleiner and Orten, published by the C. V. Mosby Company, St. Louis, 1962, Sixth Edition, page 143.

Dietary nonessential amino acids are defined as those that can be synthesized by the body and include L-tyrosine, L-arginine, L-alanine, L-histidine, L-proline, L-serine, glycine, L-cysteine, L-cystine. These nonessential amino acids are preferably included depending on the patient.

Renal disease is defined as a blood creatinine greater 1.2 mg/dl or a blood urea greater than about $30\pm5$ mg/dl. Cancer cachexia is defined as a loss of body weight of more than 15% of ideal body weight in a cancer bearing patient.

In renal patient's fat emulsions are contraindicated, because a main characteristic of these patients is an attenuated removal of endogenous fat from the blood together with a fatty liver. Exogenous fat emulsions are also cleared and utilized poorly thus increasing like risk of infarction and further melabolic deterioration.

The peripheral vein administration of our invention in a cancer patient would provide simple and mostly efficient method by which protein loss can be stopped and a repletion of body protein can be achieved.

The following examples further describe the invention.

All temperatures are in degrees F. and g/l means grams/liter.

EXAMPLE 1

A sterile, nonpyrogenic, stable solution suitable for intravenously infusing into a peripheral or central vein of critically illtraumatized patients is prepared from pure crystalline amino acids (in the L-form) and anhydrous xylitol, which are dissolved in distilled water in the following concentrations:

|  | g/l | mole/l |
|---|---|---|
| xylitol | 50.000 | 0.329 |
| Amino Acids |  |  |
| L-Isoleucine | 4.08 | 0.031 |
| L-Leucine | 4.08 | 0.031 |
| L-Valine | 3.64 | 0.031 |
| L-Tryptophan | 0.51 | 0.0054 |
| L-Phenylalanine | 1.69 | 0.102 |
| L-Lysine Acetate (base, 2.85) | 4.03 | 0.0195 |
| L-Methionine | 0.63 | 0.00422 |
| L-Threonine | 1.91 | 0.0160 |
| L-Arginine | 2.54 | 0.0146 |
| L-Alanine | 3.00 | 0.0336 |
| L-Histidine | 1.02 | 0.0066 |
| L-Proline | 3.39 | 0.0295 |
| L-Serine | 2.12 | 0.0202 |
| Glycine | 2.35 | 0.0313 |
| L-cysteine HCl.H$_2$O (base, 0.007) | 0.015 | 0.000097 |

In the foregoing formula, the ratio of essential amino acids to total amino acids is about 58%, and the ratio of branched chain amino acids to total amino acids is about 34%.

To this solution is added, 1.152 g/l of 50% phosphoric acid to adjust the pH to a more physiologic pH (approximately 6.8) and to serve as a source of phosphorous, an important nutrient. The volume is then brought to the desired volume with distilled water and sodium bisulphate U.S.P., 1.0 g/l, is added and stirred until dissolution is complete. The solution is then filtered and filled into appropriate containers for intravenous fluids and steam sterilized at 250° F. for 10 minutes.

In order to induce a catabolic state in an animal model 26 male Sprague Dawley CD rats (270 g) received a 25% third degree burn of their back. Over the period of resuscitation until 5 p.m. of the same day all animals received a 0.9% saline infusion. The rats were then randomly assigned to one of three hypocaloric diets for 4 days.

Group I received 12.5 g amino acids (AA)/kg BW.Day.

Group II received 12.5 g AA+50 kcals/kg BW.day as glucose.

Group III received 12.5 g AA+50 kcals/kg BW.day as xylitol.

BW means bodyweight.

$U_{-14}C$-glucose was infused over the last 4 hours of the study.

During the 4 days study period, daily urine production was collected to determine nitrogen excretion in the three groups. At the end of the study the animals were sacrificed and blood collected for plasma substrate evaluation.

Table I summarizes cumulative nitrogen excretion during the four days acid oxidation the greatest amount of nitrogen was wasted in this group. Providing only amino acids during partial parenteral feeding (PPR) maintains trauma induced flux of amino acids from peripheral to visceral organs as can be seen in the higher liver total protein content 100 g BW in Group I. The key to this metabolic response is only gradual increases in blood insulin levels during nutrient uptake as can be seen in Group I. A classic attenuation of the metabolic response to trauma by hypocaloric amounts of glucose can be derived from the results in Group II. Hypocaloric glucose infusion was associated with the significantly highest blood insulin levels and glucose oxidation rate. Due to the higher insulin levels $\beta$-hydroxybutyrate formation was significantly lower compared to Group I. The improved nitrogen balance in Group II compared to Group I was achieved at the expense of less protein incorporation in the liver as a sign of enhanced protein synthesis in peripheral organs, like the muscle. The data of Group I and II reveals the influence of the two current state of the art intravenous nutrition therapy forms on post-traumatic metabolism.

The principal metabolic effects of the here-presented invention is to moderate insulin and blood glucose levels, to maintain a certain amount of nutrient flux from peripheral to visceral organs and to reduce gluconeogenesis.

In Table 1 it can be seen, that the cumulative nitrogen balance on all post-traumatic days was significantly better in rats receiving hypocaloric amounts of xylitol

|  | Cumulative Nitrogen Balance (gm) | | | |
| --- | --- | --- | --- | --- |
|  | Day 1 | 1 + 2 | 1 + 2 + 3 | Cum. Bal. |
| Group I | −0.05 ± 0.01 | −0.22 ± 0.04 | −0.32 ± 0.03 | −0.49 ± 0.06 |
| Group II | −0.04 ± 0.01 | +0.07 ± 0.06* | −0.01 ± 0.08* | −0.16 ± 0.10* |
| Group III | +0.07 ± 0.03* | +0.26 ± 0.06+* | +0.26 ± 0.07+* | +0.21 ± 0.08+* |

*p 0.05 vs Group I; + p 0.05 vs Group II

The results shown in Table 1 clearly demonstrate that hypocaloric infusion of xylitol+AA is superior to either only amino acid or hypocaloric glucose provision in preserving body protein after trauma. On all post-traumatic days the nitrogen excretion on day 1 and the cumulative nitrogen excretion on day 2, 3 and 4 were significantly less in the group receiving hypocaloric amounts of xylitol compared to the two other groups. This protein preserving ability of xylitol during hypocaloric feeding is a unique and important finding for the treatment of the severely ill, who often die due to lack of protein preservation.

In order to obtain parameters revealing the mechanisms of the protein sparing ability of xylitol the following substrates and hormones were analyzed in the plasma and liver tissue.

together with amino acids compared to either only amino acid or amino acid and hypocaloric glucose feeding. This feeding is unique and has never before been demonstrated for any other equicaloric replacement of glucose by any other energy source. Hypocaloric amounts of xylitol reduce gluconeogenesis as can be derived from the data in Table 2. Glucose flux represents overall glucose turnover in the body. In Group I, glucose flux of 548.2 umol/hr is maintained by the conversion of AA to glucose in the liver. Hypocaloric amounts of glucose are known to reduce gluconeogenesis as can be seen in Group II with a glucose flux of 135.6 umol/hr. Xylitol though not only reduces gluconeogenesis significantly more than the glucose group, but also maintains liver protein significantly higher than glucose. The liver is the most important organ in pre-

|  | Glucose mg/dl | Gluc. Oxidat. umol/h | Endogenous Gluc. Flux. umol/h | B-OH-butyr. mM | Insulin uU/ml | Liver Tot. Prot./100 g BW |
| --- | --- | --- | --- | --- | --- | --- |
| Group I | 143 ± 4 | 153 ± 6 | 548.2 ± 104.7 | 0.29 ± 0.09 | 15.7 ± 0.6 | 0.74 ± 0.02 |
| Group II | 148 ± 11 | 256 ± 18* | 135.6 ± 40.7* | 0.13 ± 0.02* | 22.9 ± 0.6* | 0.64 ± 0.04 |
| Group III | 124 ± 5* | 190 ± 13+* | 28.2 ± 10.6+* | 0.21 ± 0.03 | 18.3 ± 0.4+ | 0.78 ± 0.03+ |

*p < 0.05 vs Group I; + p < 0.05 vs Group II

Group I received only amino acid for partial parenteral feeding, these animals maintained their blood glucose level by converting amino acids to glucose during gluconeogenesis. Although $\beta$-hydroxybutyrate formation was increased in Group I as a sign of increased fatty serving glucose, protein and energy homeostasis. Xylitol in Group III moderates blood glucose, reduces gluconeogenesis and preserves body protein more efficiently thereby increasing the incorporation of protein into the liver.

The lower insulin level in Group III indicates an insulin independent mechanism for the mproved protein preservation during xylitol infusion, indicating a direct pharmacological property of this substance.

EXAMPLE 3

The body protein preserving ability of xylitol during hypocaloric peripheral intravenous feeding was evaluated in critically ill patients. Patients entering this study had suffered a severe injury or had extensive gastrointestinal surgery requiring intensive care therapy.

The patients received either 185 g/kg BW.day of glucose (Group I) or 185 g/day of xylitol (Group II) as energy source. Both groups received 17.1 g nitrogen per day as amino acids. The infusion rates are related to a 70 kg BW patient. Oral nutrient intake was contraindicated in all patients.

| | Nitrogen Balance | | | | | |
|---|---|---|---|---|---|---|
| | Day 1 | Day 2 | Day 3 | Day 4 | Day 5 | Cumul g N |
| Group I (N = 9) | −13.6 ± 3.2 | −15.2 ± 3.1 | −17.8 ± 2.4 | −17.1 ± 2.8 | −16.6 ± 3.4 | −80.3 |
| Group II (N = 10) | −8.2 ± 1.6 | −8.6 ± 2.0 | −10 ± 1.8 | −9.1 ± 2.2 | −8.8 ± 2.5 | −44.7 |

Partial parenteral feeding in these patients was initiated in the intensive care unit after vital organ functions like cardiac performance, respiration, and urine production had been treated. During the first days following severe injury, the use of glucose during parenteral feeding is accompanied by an increase in the levels of stress hormones, catecholamines, and cortisol, thereby increasing resting energy expenditure, reducing fatty acid oxidation, promoting lipoprotein synthesis, stimulating $CO_2$ production, reducing visceral protein synthesis, inducing hepatic dysfunction And causing water retention. We, therefore, used only hypocaloric amounts of glucose during the first five days of intravenous feeding, in order not to further alter the metabolic state of the patients. By giving a second group of comparable patients an equicaloric amount of xylitol as energy source, we were able to obtain a direct comparison of the nitrogen preserving ability between the most frequently used carbohydrate for intravenous use, glucose, and our newly introduced carbohydrate, xylitol. On all posttraumatic days, nitrogen excretion was less in patients receiving hypocaloric amounts of xylitol with amino acids. The cumulative nitrogen excretion in g N was 44.4% less in Group II. One g Nitrogen is equal to 6.25 protein. A cumulative nitrogen loss of 80.3 g is equal to 501 g pure protein in Group I. The protein loss in Group II amounts to 279 g. The amount of loss of precious protein during the initial days following trauma has an impact on the outcome of a patient. During the early phase of trauma, the organ systems with a high daily protein turnover like the liver, gut, pancreas, immune system, and the kidneys contribute most to overall protein loss. The adequate functioning of these organ systems is even more vital during a state after trauma.

The gut needs to initiate oral nutrient uptake as soon as possible, absorbing larger nutrient quantities than during the normal state. The liver needs to excrete toxic endogenous and exogenous substrates; the pancreas needs to provide more insulin, and excretory juice for digestion; the immune system takes over its responsibility for host defense and induction of fever and the kidneys need to excrete metabolites derived from catabolic processes, while at the same time spare electrolytes and fluid.

The nitrogen sparing ability of hypocaloric amounts of xylitol with amino acids will help maintain adequate organ function in those tissues rendered protein depleted by conventional nutrition therapy.

A sterile pharmaceutical parenteral preparation according to this invention may comprise the following ingredients:

| | g/l |
|---|---|
| xylitol | 30–80 |
| L-isoleucine | 1–6 |
| L-leucine | 1–6 |
| L-valine | 0.85–5 |
| L-tryptophan | 0.11–070 |
| L-phenylalanine | 0.3–2 |
| L-lysine acetate | 1–6 |
| L-methionine | 0.15–0.8 |
| L-threonine | 0.5–3.0 |
| L-arginine | 0.67–4 |
| L-alanine | 0.67–4 |
| L-histidine | 0.25–1.5 |
| L-proline | 0.82–5.0 |
| L-serine | 0.5–3.0 |
| glycine | 0.67–4 |
| L-cysteine $HCl.H_2O$ | 0.003–0.02. |

What is claimed is:

1. A method of treating a human patient suffering from renal failure to preserve human lean body mass comprising the peripheral venous infusion of an isotonic hypocaloric sterile aqueous preparation containing 10 to 80 grams/liter of xylitol to said human patient.

2. A method of treating a human patient receiving ventalitory support to preserve human lean body mass comprising the peripheral venous infusion of an isotonic hypocaloric sterile aqueous preparation containing 10 to 80 grams/liter of xylitol to said human.

3. A method of treating a human suffering from cancer cachexia to pressure human lean body mass comprising the peripheral venous infusion of an isotonic hypocaloric sterile aqueous infusion of an isotonic hypocaloric sterile aqueous preparation containing 10 to 80 grams/liter of xylitol to said human.

* * * * *